(12) United States Patent
Lacaze (10) Patent No.: US 9,788,920 B2
(45) Date of Patent: Oct. 17, 2017

(54) ENDOSSEOUS IMPLANT HAVING IMPROVED ANCHORAGE

(76) Inventor: Guillaume Lacaze, Montech (FR)

( * ) Notice: Subject to any disclaimer, the term of this patent is extended or adjusted under 35 U.S.C. 154(b) by 857 days.

(21) Appl. No.: 13/824,009

(22) PCT Filed: Oct. 5, 2011

(86) PCT No.: PCT/EP2011/067410
§ 371 (c)(1),
(2), (4) Date: Jun. 3, 2013

(87) PCT Pub. No.: WO2012/045787
PCT Pub. Date: Apr. 12, 2012

(65) Prior Publication Data
US 2014/0148864 A1    May 29, 2014

(30) Foreign Application Priority Data

Oct. 5, 2010  (FR) ...................................... 10 58048

(51) Int. Cl.
*A61C 8/00* (2006.01)
*A61B 17/68* (2006.01)
*A61B 17/84* (2006.01)

(52) U.S. Cl.
CPC .......... *A61C 8/0033* (2013.01); *A61B 17/686* (2013.01); *A61B 17/844* (2013.01)

(58) Field of Classification Search
CPC .... A61C 8/0033; A61B 17/844; A61B 17/686
See application file for complete search history.

(56) References Cited

U.S. PATENT DOCUMENTS 5,004,421 A * 4/1991 Lazarof ............... A61C 8/0033
                                                    433/173
5,087,199 A   2/1992 Lazarof
6,783,361 B2 * 8/2004 Huge ..................... A61C 7/10
                                                    433/7

(Continued)

FOREIGN PATENT DOCUMENTS

DE      29619163        3/1998
FR       2467584        4/1981
KR     20040063528      7/2004

OTHER PUBLICATIONS

International Search Report issued for PCT/EP2011/067410; dated Dec. 29, 2011, 4 pages.

*Primary Examiner* — Heidi M Eide
(74) *Attorney, Agent, or Firm* — Norton Rose Fulbright US LLP (57) ABSTRACT

The invention relates to an endosseous implant capable of being implanted into osseous tissue. The implant comprises an attachment device (3), comprising:
  a so-called gripping portion (31) for gripping the osseous tissue,
  a so-called expansion portion (32), said two portions being mobile in relation to each other,
  engaging mechanical connection means (33, 33a, 33b), located on the gripping portion (31) on the one hand and on the expansion portion (32) on the other hand, such that the relative mobility of the two portions has at least one degree of freedom, and such that a relative movement of said two portions causes an extension of the gripping portion, said extension causing the gripping portion to engage with the osseous tissue.
The endosseous implant can in particular be used in the dental field.

3 Claims, 9 Drawing Sheets

(56) References Cited

U.S. PATENT DOCUMENTS

| | | |
|---|---|---|
| 2005/0042574 A1 | 2/2005 | Lazarof |
| 2010/0114314 A1 | 5/2010 | Lomicka et al. |
| 2011/0111369 A1* | 5/2011 | Laster ................ A61B 17/0401 433/174 |
| 2011/0172774 A1* | 7/2011 | Varela .................... A61F 2/447 623/17.16 |
| 2011/0207080 A1* | 8/2011 | Maadi ................ A61C 13/0001 433/148 |

* cited by examiner

Fig. 4a coupe C-C

Fig. 4c coupe A-A

Fig. 4b

Fig. 5a coupe C-C

Fig. 5c coupe A-A

Fig. 6b coupe A-A

ENDOSSEOUS IMPLANT HAVING IMPROVED ANCHORAGE

The invention relates to the field of endosseous implants intended for dental, orthopaedic, surgical or osteoplastic applications such as dental, hip, knee or joint implants.

Endosseous implants are used in surgery to implant a prosthetic device in a patient, for example a dental prosthesis. Such endosseous implants are mainly used in the dental field, however are also used in reconstructive surgery for example. These fields of application are provided for the purpose of illustration only and do not limit the scope of this invention.

An endosseous implant is generally constituted from a body, elongated in shape, intended to be implanted in a housing formed in osseous tissue, such as the jaw bone in dental applications, and comprises anchoring means for anchoring the implant into the osseous tissue on the one hand and means for receiving a prosthetic device on the other hand, such a device capable of being an inlay core, a gingiva abutment or an orthodontic band, etc.

This type of endosseous implant must be capable of being easily inserted into osseous tissue and of being strongly bonded to the latter.

It must also be easy to manufacture at a low cost.

Currently, the installation of a full prosthetic assembly (comprised from an endosseous implant and an associated prosthetic device) is relatively long. Firstly, the endosseous implant is positioned in the housing formed within the osseous tissue. This positioning of the endosseous implant within the osseous tissue is always followed by a period of osseointegration generally lasting 5 to 6 months so as to enable the bone to adhere to the endosseous implant. Secondly, according to the application and said endosseous implant, the latter becomes the holder of a specific prosthetic device.

This osseointegration period that takes place before the prosthetic device can be attached onto the endosseous implant is generally poorly tolerated by the patient that has received the endosseous implant, mainly in the case of an endosseous dental implant. Indeed, during this period, as no prosthetic device can be placed onto the endosseous implant, this area remains empty and the teeth suffer from a non-aesthetic appearance, above all when this area is located near to the incisors.

Another disadvantage of the current endosseous implant is the connection between the endosseous implant and the prosthetic device, which has insufficient sealing. This may lead to problems involving bacteriological contamination or to the infiltration of impurities within the endosseous implant and cause inflammation of the gums and potentially bone deterioration.

Another disadvantage of the current endosseous implant is the problem of the quality of its anchoring in the osseous tissue.

Indeed, anchoring an endosseous implant, during its insertion by the practitioner in the housing previously made within the osseous tissue, is currently only performed using anchoring means arranged on an outer surface of the body.

Anchoring means are, for example, impaction means or preferably screwing means, generally self-tapping. In a general manner, these anchoring means implement raised attachments, arranged to maintain the endosseous implant in position within the bone during its installation. Such raised attachments are, for example, comprised from a thread for anchoring means by screwing, and/or from ring-shaped members for anchoring means by impaction.

However, in the dental field, the endosseous implant is often subject to pressure and/or significant stresses and/or excessive loads. Therefore, the endosseous implant can, for example, suffer inadvertent or accidental rotations following mastication or caused by the patient's tongue, which may cause the endosseous implant to unexpectedly move outside of the osseous tissue.

These anchoring means are therefore insufficient in preventing all risks of the spontaneous removal of the endosseous implant during the osseointegration period.

A real need therefore exists for improving the sealing and anchoring of current endosseous implants, while maintaining easy implant manufacture at a low cost.

The purpose of this invention is to overcome the aforementioned disadvantages and thus relates to an endosseous implant capable of being implanted into osseous tissue and comprising a fastening device including:
- a so-called gripping portion for gripping said osseous tissue,
- a so-called expansion portion, said two portions being mobile in relation to each other,
- engaging mechanical connection means, located on the gripping portion on the one hand and on the expansion portion on the other hand, such that the relative mobility of the two portions has at least one degree of freedom, and such that a relative movement of said two portions causes an extension of the gripping portion, said extension causing the gripping portion to engage with the osseous tissue.

The mechanical connection means are capable of connecting the gripping portion and the expansion portion together.

Therefore the endosseous implant, in an initial state, i.e. before its insertion into a receiving housing created in the osseous tissue and adapted to suit the dimensions of the endosseous implant, has a fastening device for connection with the gripping portion not showing any extension. During the introduction of the endosseous implant in the housing, the fastening device is not in contact with the walls of said housing.

When the expansion portion is in contact with the walls of the housing, a relative movement between said two portions is created causing an extension of the gripping portion until said gripping portion is anchored into the walls of the housing of the osseous tissue.

The presence of such a fastening device on the endosseous implant thus improves the anchoring of said endosseous implant in the osseous tissue by rotational and translational immobilisation in said osseous tissue. The endosseous implant according to the invention is not therefore subject to accidental or inadvertent rotations or translations capable of causing the involuntary removal of the endosseous implant from the housing of the osseous tissue unlike endosseous implants in the prior art.

Preferably, the endosseous implant as proposed herein can be applied in the dental field for installing dental prostheses, however the endosseous implant can also be applied in many other fields for example for the purpose of illustration only and not limiting the scope of the invention, orthopaedic, surgical and osteoplastic fields for installing hip, knee or joint prostheses.

According to the preferred embodiments, the invention also has the following characteristics, taken individually or in any combination technically possible.

According to one characteristic of the invention, the endosseous implant comprises a body, elongated in shape along a longitudinal axis. Preferably, said body is located between a first end, referred to as an exosseous end and a second end, referred to as an endosseous end.

Preferably, the fastening device is connected to one of the ends of said body, preferably to the endosseous end.

In one embodiment of the endosseous implant, said endosseous implant comprises, at an outer surface of the body, means for anchoring the implant into the osseous tissue.

In one preferred embodiment of the anchoring means, said anchoring means are screwing means and comprise a thread on the outer surface.

In one embodiment of the endosseous implant, said endosseous implant comprises, at the exosseous end, first connection means capable of engaging with a torque wrench for inserting the endosseous implant into the housing, and second connection means capable of engaging with a prosthetic device.

In the examples of embodiment of the two connection means, said means can be polygonal in shape, with inner or outer threads or have any shape enabling a prosthetic device to be maintained in place.

According to one characteristic of the invention, the at least one degree of freedom between the gripping portion and the expansion portion is a translation along the longitudinal axis. The gripping portion and expansion portion are therefore mobile in relation to each other by translating movement along the longitudinal axis. This translating movement enables the gripping portion to be transversally extended in relation to said longitudinal axis until said gripping portion grips the walls of the housing of the osseous tissue.

According to another characteristic of the invention, the gripping portion is elastically deformable and comprises at least two longitudinal slots capable of allowing for a more significant extension of said gripping portion.

According to another characteristic of the invention, the gripping portion comprises, at an outer surface, immobilising means for rotationally and/or translationally immobilising said endosseous implant within the osseous tissue after implantation.

In one example of embodiment of the immobilising means, said immobilising means are a thread, asperities, teeth or protrusions, preferably with a triangular profile.

In a first embodiment of the endosseous implant, the gripping portion is connected to the body and comprises a cavity for receiving the expansion portion.

According to one advantageous characteristic of this first embodiment, the expansion portion comprises, preferably at one end opposite the endosseous end, cavity extension means capable of extending an opening within said cavity and of causing the gripping portion to extend until anchored into the walls of the housing of the osseous tissue.

Alternatively to this first embodiment, the expansion portion comprises, at one end near to the body, a recess having an inner thread for moving said expansion portion in translation towards the body.

In another embodiment of the endosseous implant, the expansion portion is in this case attached to the body and the gripping portion is arranged circumferentially around said expansion portion.

According to one advantageous characteristic of this other embodiment, the connection means are engaging screwing means and the fastening device comprises engaging reverse-lock means capable of preventing rotation between the gripping portion and the expansion portion in a direction opposite to that allowed by said screwing means.

The screwing means allow for the screwing, according to a given direction of rotation, of one portion in relation to the other portion of the fastening device. The reverse-lock means prevent rotation between the two portions in the opposite direction.

According to one advantageous characteristic of this other embodiment, the engaging reverse-lock means comprise on the one hand, at an outer surface of the expansion portion, a first outer peripheral toothing and on the other hand, at an inner surface of the gripping portion, a second outer peripheral toothing.

In one example of embodiment of the toothings, said outer peripheral toothings of the gripping portion and of the expansion portion have a saw-toothed cross profile with asymmetrical sides, the profile comprising upwards sloping sides and downwards sloping sides, each upwards sloping side being connected to a downwards sloping side by a substantially sharp cutting edge.

The outer peripheral toothings are therefore positioned in relation to each other in a manner so as to only be able to move in relation to each other in a single direction of rotation.

In the screwing direction, the upwards sloping sides of the gripping portion slide against the upwards sloping sides of the expansion portion to enable the relative rotational movement, and thus the translational movement along the longitudinal axis of the implant, of the gripping portion in relation to the expansion portion.

In the event of unscrewing, i.e. screwing in the opposite direction of rotation, the downwards sloping sides of the gripping portion abut against the downwards sloping sides of the expansion portion, thus blocking unscrewing movements.

According to one advantageous characteristic of this other embodiment, the expansion portion comprises longitudinal grooves capable of enabling the implant to be locked in the screwing direction upon the completed compression of said implant within the osseous tissue.

The implant is thus immobilised in rotation, in the screwing direction by the longitudinal grooves and in the unscrewing direction by the reverse-lock means.

According to one advantageous characteristic of this other embodiment, to ease machining of the fastening device, the engaging screwing means and the reverse-lock means are separate from each other.

Preferably, the endosseous implant is manufactured using appropriate biocompatible, surgically acceptable material for example titanium or any other implantable material. The endosseous implant is manufactured based on a sketch using known methods, for example by moulding, sintering or machining.

Alternatively, the endosseous implant can be manufactured from zirconium using zirconium oxide. Preferably, this is dental quality or surgical quality zirconium. Zirconium endosseous implants have a biocompatibility rate that far exceeds that of titanium and lead to very fast consolidation and osseointegration, approximately 4 times quicker than that of titanium endosseous implants.

Zirconium endosseous implants prevent electrically conductive contacts from occurring with the dental nerve and improve aesthetic appearance as this cannot be seen underneath the wall of the dental prosthesis, which is often thin and translucent.

Endosseous implants according to the invention are therefore very solid, have excellent osseointegration capacities and incur minimal trauma during installation.

The invention shall now be described in more detail within the scope of preferred embodiments, which in no way limit the invention, represented in FIGS. 1a to 3d, wherein:

FIG. 3e illustrates a zoom of the endosseous implant in FIG. 3d at the level of the expansion portion, FIGS. 4a to 4c respectively represent a front view of the implant, a longitudinal cross-section and a transversal cross-section of the fastening device according to an alternative of the third embodiment of the invention, in an initial state, before insertion into the housing of an osseous tissue, FIGS. 5a to 5c respectively represent a front view of the implant, a longitudinal cross-section and a transversal cross-section of the fastening device according to an alternative of the third embodiment of the invention, in an extended state, after insertion into the housing of an osseous tissue.

The different embodiments of the endosseous implants according to the invention are described hereinbelow using the example of dental application, however in no way limit the scope of the invention.

Dental endosseous implants are intended for implantation by a practitioner into the osseous tissue of the patient's jaw, for example a mandibular or maxilla bone.

The endosseous implants, hereinafter referred to as implants 1, represented in FIGS. 1a to 3d and illustrating three embodiments all comprise a portion forming a body 2 formed from a cylindrical portion, substantially revolving around a longitudinal axis 11, and a transversal cross-section, preferably circular in shape.

The body 2 comprises a first end, known as an endosseous end 21 and a second opposite end, known as an exosseous end 22.

In a routine manner, the implant is inserted into a housing 61 previously created in the osseous tissue 6 of the jaw so as to leave the exosseous end 22 of the implant 1 showing at the surface of the gum, thus enabling the installation of a prosthetic device (not represented in the figures), such as a dental prosthesis or an inlay.

The exosseous end 22 of the body forms a connector head designed to receive the prosthetic device and comprises first connection means 25 capable of engaging with a screwing tool for inserting the implant 1 into the housing 61.

The connection means 25 are, for example an inner threaded and tapped channel in the body opening up at the exosseous end 22.

In another example, the connection means are a polygonal inner cavity, typical hexagonal in shape, for receiving a screwing tool such as a screwdriver or allen key.

At an outer surface 24, the body 2 comprises anchoring means 23.

Preferably, the anchoring means 23 are screwing means and comprise a thread with a determined, constant pitch, for example between 0.25 and 2 mm, on the outer surface 24 (the thread is clearly represented in FIGS. 2a, 2b, 3a, 3b, 8a and 8b).

The anchoring means 23 are distributed throughout all or part of a length of the body, preferably substantially over the entire length as illustrated in the figures.

The presence of the thread 23 on the implant 1 generates a helical movement for the entire implant. This helical movement locks the implant in position by compressing it in the osseous tissue of the jaw.

The presence of the thread 23 on the implant also advantageously significantly increases the surface area of the implant for osseointegration.

The body 2 extends, at the endosseous end 21 by a fastening device 3, with an overall frustoconical shape, narrowing as it extends from the body 2.

The fastening device 3 comprises:
  a first portion, known as a gripping portion 31 for gripping the osseous tissue,
  a second portion, known as an expansion portion 32,
  engaging mechanical connection means 33, 33a, 33b between the gripping portion 31 and the expansion portion 32.

The mechanical connection means 33, 33a, 33b are positioned on the one hand at the level of the gripping portion 31 and on the other hand at the level of the expansion portion 32.

The mechanical connection means 33, 33a, 33b provide for the relative mobility of the two portions 31, 32 with at least one degree of freedom. Therefore, for all of the embodiments described herein, the two portions 31, 32 are mobile in relation to each other by translation along the longitudinal axis 11.

The translation motion generates a relative movement of said two portions, thus causing the gripping portion 31 to extend radially in relation to the longitudinal axis 11. The radial extension causes the gripping portion 31 to grip the lateral walls 62 of the housing 61 in the osseous tissue.

The fastening device 3 may have different forms. For the purpose of illustration only and in no way intended to limit the scope of the invention, three forms shall now be described.

Figure 1A:
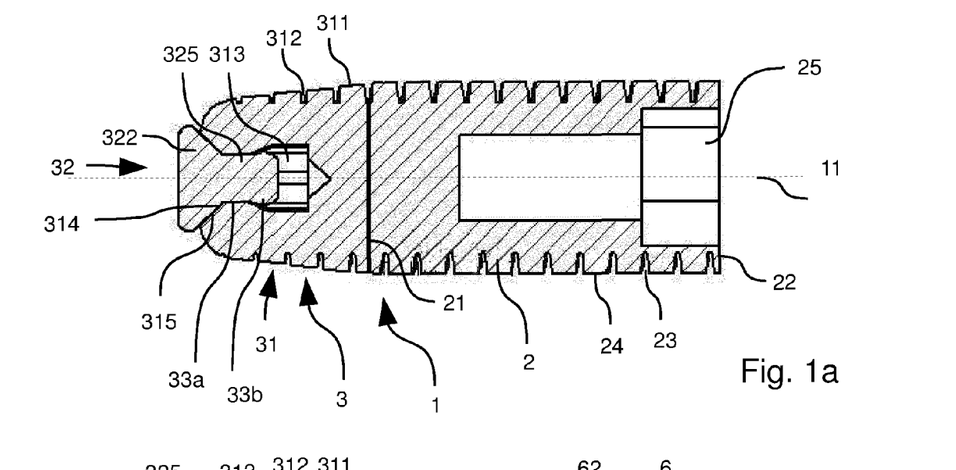
FIG. 1a schematically represents a longitudinal cross-section of an endosseous implant according to a first embodiment of the invention, in an initial state, before insertion into a housing of an osseous tissue, FIG. 1b schematically represents a longitudinal cross-section of the endosseous implant according to a first embodiment of the invention, in an extended state, after insertion into a housing of an osseous tissue.
Figure 1B:
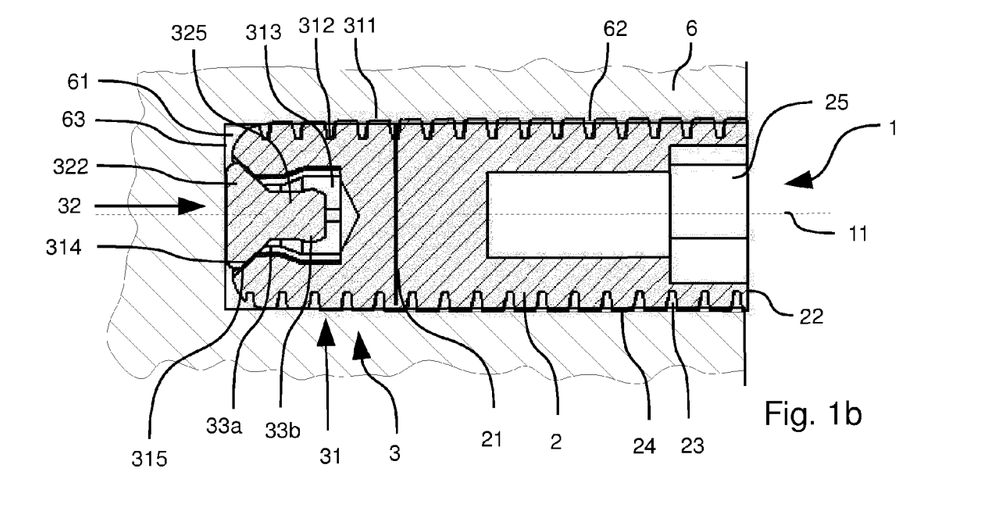
Figure 1C:
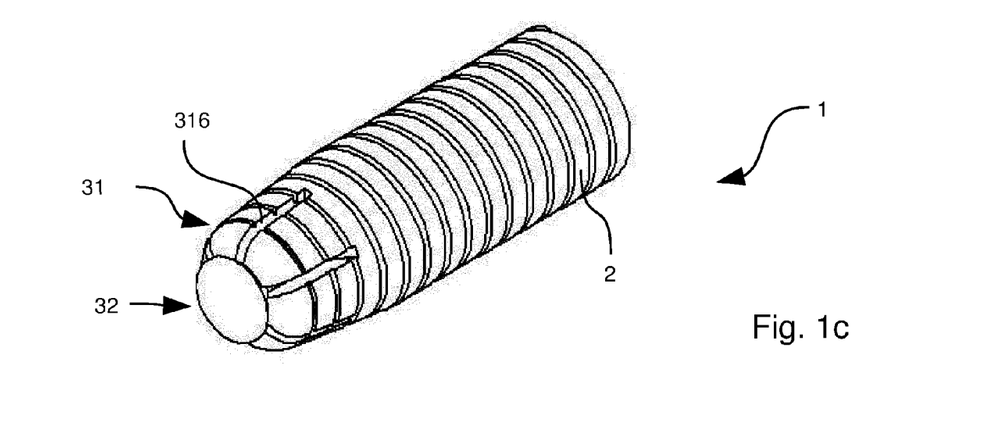
FIG. 1c represents a perspective view of the osseous implant according to the first embodiment of the invention, in an initial state.
Figure 2A:
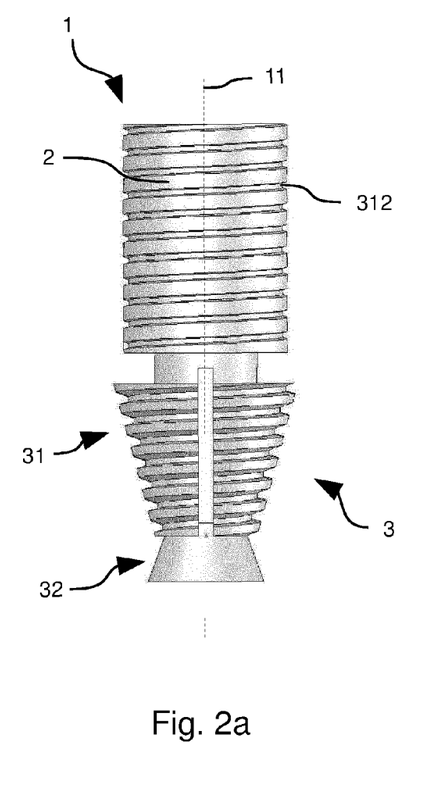
FIG. 2a represents a front view of an endosseous implant according to a second embodiment of the invention, in an initial state, before insertion into a housing of an osseous tissue.
Figure 2B:
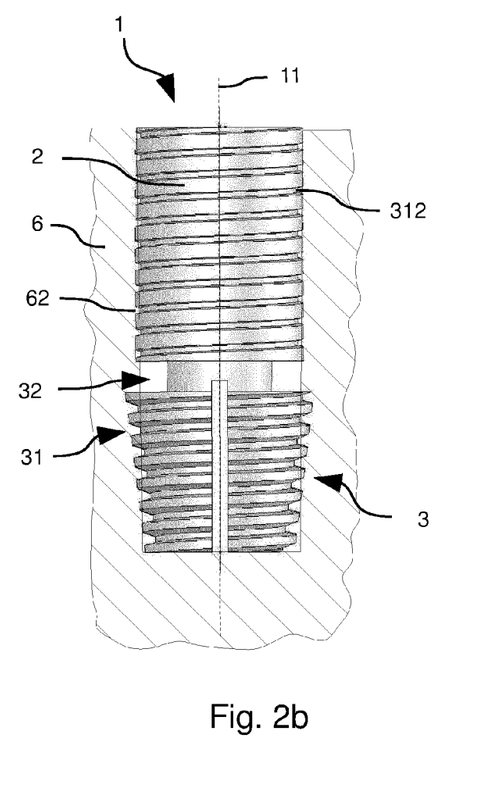
FIG. 2b represents a front view of the endosseous implant according to a second embodiment of the invention, in an extended state, after insertion into a housing of an osseous tissue.
Figure 2C:
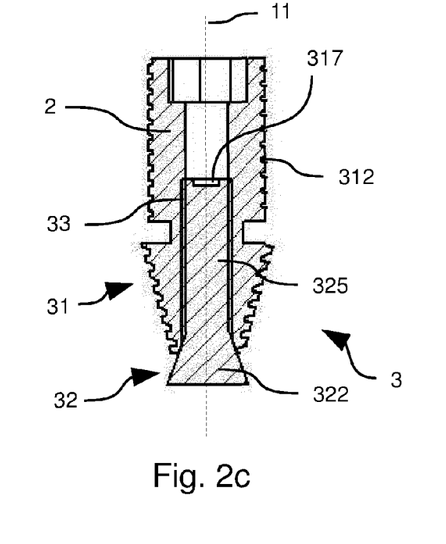
FIG. 2c represents a longitudinal cross-section of the implant in FIG. 2a, FIG. 2d represents a longitudinal cross-section of the implant in FIG. 2b.
Figure 2D:
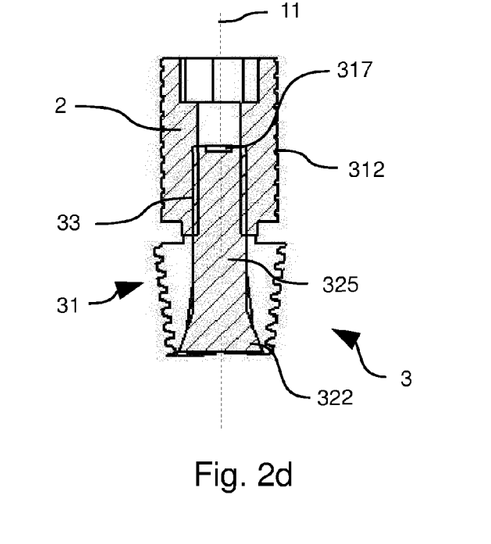

A first embodiment of the fastening device 3 is represented in a schematic manner in FIGS. 1a and 1c.

The gripping portion 31, with an overall frustoconical shape, is connected to the endosseous end 21 of the body 2 of the implant 1 and comprises a cavity 313 for receiving the expansion portion 32.

In this example, the cavity 313 is preferably cylindrical in shape, substantially revolving around the longitudinal axis 11 of the implant, with an opening 314 at one end opposite the body.

The expansion portion 32 comprises a substantially cylindrical portion 325, with a diameter less than an inner diameter of the cavity 313.

Said cylindrical portion 325 ends, at one end located near to the opening 314 of the cavity 313, with an extension means 322 of the cavity 313, capable of extending the opening when the expansion portion 32 moves along the longitudinal axis in relation to the gripping portion 31.

In the example illustrated in FIGS. 1a and 1b, the extension means 322 are, for example, preferably frustoconical in shape, extending from the cylindrical portion 325.

The engaging connection means 33a, 33b maintain the expansion portion 32 in the gripping portion 31. As illustrated in FIGS. 1a and 1b, these for example consist in:
- on the one hand, at the level of the gripping portion 31, a convex, ring-shaped protrusion 33a on an inner surface of the cavity 313, locally reducing the inner diameter of said cavity,
- on the other hand, at the level of the expansion portion 32, a convex, ring-shaped protrusion 33b at the surface of the cylindrical portion 325, locally increasing the outer diameter of said cylindrical portion.

In an initial state, before inserting the implant 1 into the housing 61 of the osseous tissue 6, the cylindrical portion 325 of the expansion portion 32 is positioned in the cavity 313.

The implant, in an initial state, is represented by FIGS. 1a and 1c.

Advantageously, to ease the relative translation movement between the expansion portion and the gripping portion, the opening 314 of the cavity 313 comprises a chamfer 315 with a shape complementing an outer frustoconical shape of the extension means 322.

The gripping portion 31 is made from biocompatible material with elastic properties enabling it, when the gripping portion is elastically stressed, to radially extend between its initial position, before introduction in the housing, and its deployed position, after introduction in the housing.

In this first embodiment, the implant is preferably made from titanium.

Advantageously, the gripping portion also comprises longitudinal slots 316 opening up at one end located near to the opening 314 of the cavity 313, said longitudinal slots being capable of allowing for a more significant extension of said gripping portion. In the non-limitative example in FIG. 1c, four longitudinal slots 316 are represented.

Although four longitudinal slots are illustrated in FIG. 1c, these slots are not limited in number to that described and illustrated. It is therefore possible, without leaving the scope of the invention, to manufacture a gripping portion with two or three longitudinal slots or more.

To improve the grip of the implant 1 on the walls 62 of the housing 61 in the osseous tissue, the gripping portion 31 comprises immobilising means 312 rotationally and translationally immobilising the gripping portion 31 on all of part of its outer surface 311.

In one example of embodiment of the immobilising means 312, as illustrated in FIGS. 1a to 1c, said means are a thread.

In another example of embodiment of the immobilising means 312, said means are a plurality of teeth extending radially towards an outer edge of the gripping portion.

In another example of embodiment of the immobilising means, said means are a plurality of blades or protrusions, randomly oriented, with a transversal cross-section preferably triangular in shape with a sharp cutting edge.

Mode of Operation of this First Embodiment of the Implant

The implant 1 (FIG. 1a, in an initial state) is introduced into the housing 61 of the osseous tissue 6 by screwing the anchoring means 23 into the lateral walls 62 of said housing 61 using a suitable screwing tool.

When the extension means 322 abuts against a lower wall 63 of the housing 61 opposite the former, the practitioner continues to screw. The implant 1 continues to enter the housing 61 whereas said extension means remains locked in the housing. The gripping portion 31 is mobile and moves in translation in relation to the expansion portion 32 along the longitudinal axis 11 towards the lower wall 63 of the housing 61, causing the expansion portion 32 to rise within the cavity 313 of the gripping portion towards the body 2 of the implant 1. This relative translational movement along the longitudinal axis 11 causes the opening 314 of said cavity to extend and thus causes the gripping portion to extend (FIG. 1b) until it becomes anchored into the lateral walls 62 of the housing 61.

The implant is thus immobilised both in translation and rotation.

The screwing of the implant 1 into the housing 61 of the osseous tissue advantageously generates the relative translational movement between the two portions.

Alternatively to this first embodiment of the fastening device illustrated in FIGS. 2a to 2d, the cavity 313 of the gripping portion 31 crosses the body 2 of the implant 1 and reappears at the exosseous end 22.

The cylindrical portion 325 of the expansion portion 32 also comprises, at one end located near to the body 2 of the implant 1, a recess 317 having an inner thread for moving said expansion portion in relation to the gripping portion 31 in translation along the longitudinal axis 11 towards the body.

According to one characteristic of this alternative, the fastening device 3 has, further to the translational degree of freedom, a rotational degree of freedom around the longitudinal axis.

Advantageously, the engaging connection means 33 maintaining the expansion portion 32 within the gripping portion 31 are comprised from a helical connection between an outer surface of the expansion portion 32 and the inner surface of the cavity of the gripping portion 31.

Mode of Operation of this Alternative to the First Embodiment of the Implant

The implant 1 (FIGS. 2a, 2c) is firstly introduced into the housing 61 of the osseous tissue 6 by screwing the anchoring means 23 into the lateral walls 62 of said housing 61 using a suitable screwing tool.

When the extension means 322 abut against the lower wall 63 of the housing 61, the practitioner stops screwing. The practitioner then introduces another screwing tool into the cavity 313 to the inner thread of the recess 317 of the expansion portion, said tool being capable of engaging with said inner thread, and screws the expansion portion 32. For convenience purposes for the practitioner, the pitch of the screw is a right-handed screw pitch, however a left-handed screw pitch may also be considered. The expansion portion 32 moves in relation to the gripping portion in translation along the longitudinal axis 11 in the cavity 313 of the gripping portion towards the exosseous end 22. This relative translational movement along the longitudinal axis 11 causes the opening 314 of said cavity to extend and thus causes the gripping portion to extend (FIG. 2b, 2d) until it becomes anchored into the lateral walls 62 of the housing 61.

This alternative embodiment requires a double screwing operation on the implant to immobilise the latter in translation and rotation.

In this first embodiment of the implant, regardless of the variant, for an initial body diameter of 3.5 mm, an implant can be obtained, with the elastic properties of the titanium gripping portion and after expansion, with a diameter at said gripping portion of 3.9 to 4 mm.

In a second embodiment, illustrated in FIGS. 3a to 3e and 4a to 8b, the expansion portion 32 is connected to the endosseous end 21 of the body 2 of the implant 1 and has a frustoconical shape, narrowing from said endosseous end.

The gripping portion 31 is arranged circumferentially around the expansion portion 32 and has an inner surface 318 engaging with an outer surface 327 of the expansion portion 32.

To connect the gripping portion 31 to the expansion portion 32, said expansion portion also has a shoulder 326 at its narrowest end.

The gripping portion 31 is made from biocompatible material with elastic properties enabling it, when the gripping portion is elastically stressed, to radially extend between its initial position before introduction in the housing, and its deployed position after introduction in the housing.

In this embodiment, the implant is preferably made from titanium or zirconium.

Figure 3A:
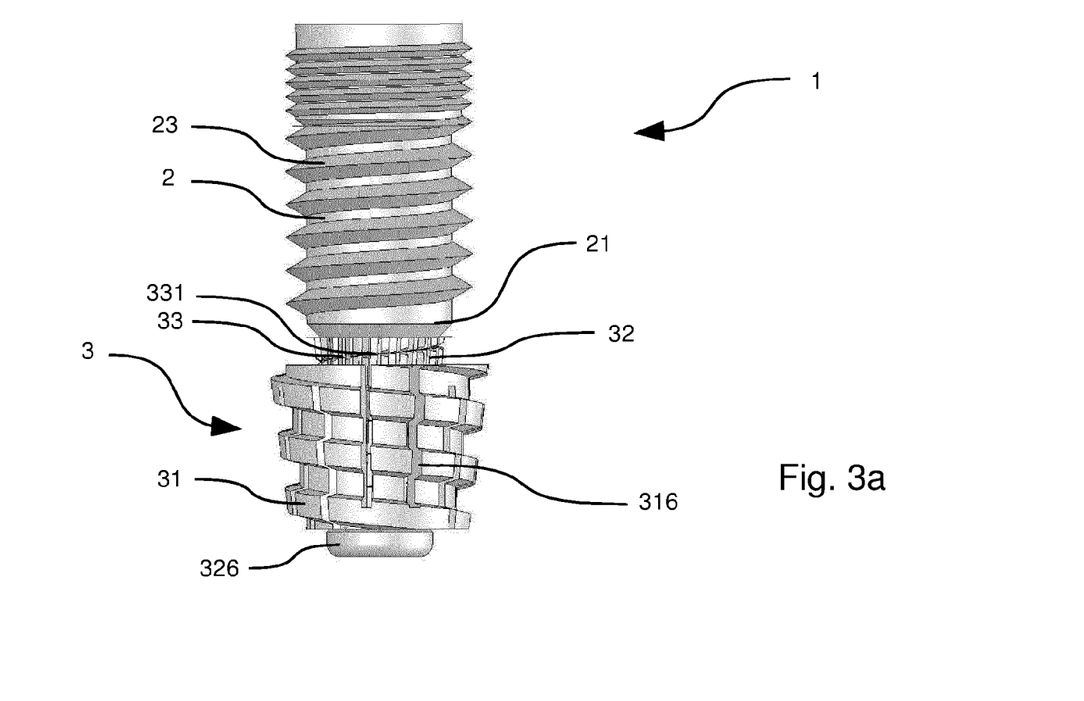
FIG. 3a represents a front view of an endosseous implant according to a third embodiment of the invention, in an initial state, before insertion into a housing of an osseous tissue.
Figure 3B:
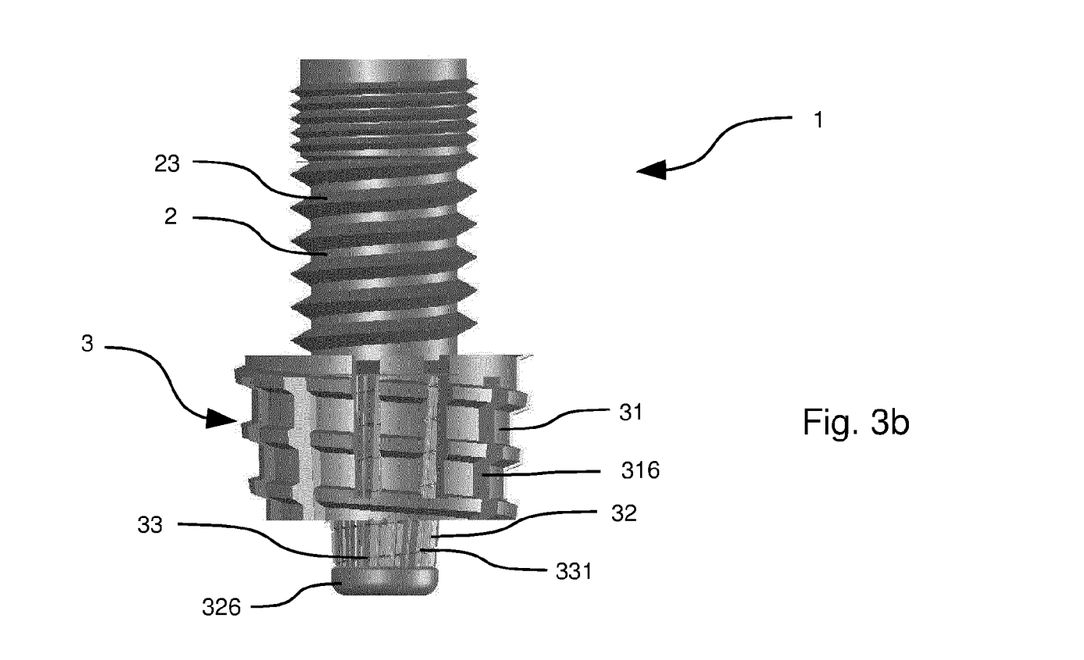
FIG. 3b represents a front view of the endosseous implant according to the third embodiment of the invention, in an extended state, after insertion into a housing of an osseous tissue.
Figures 3C, 3D:
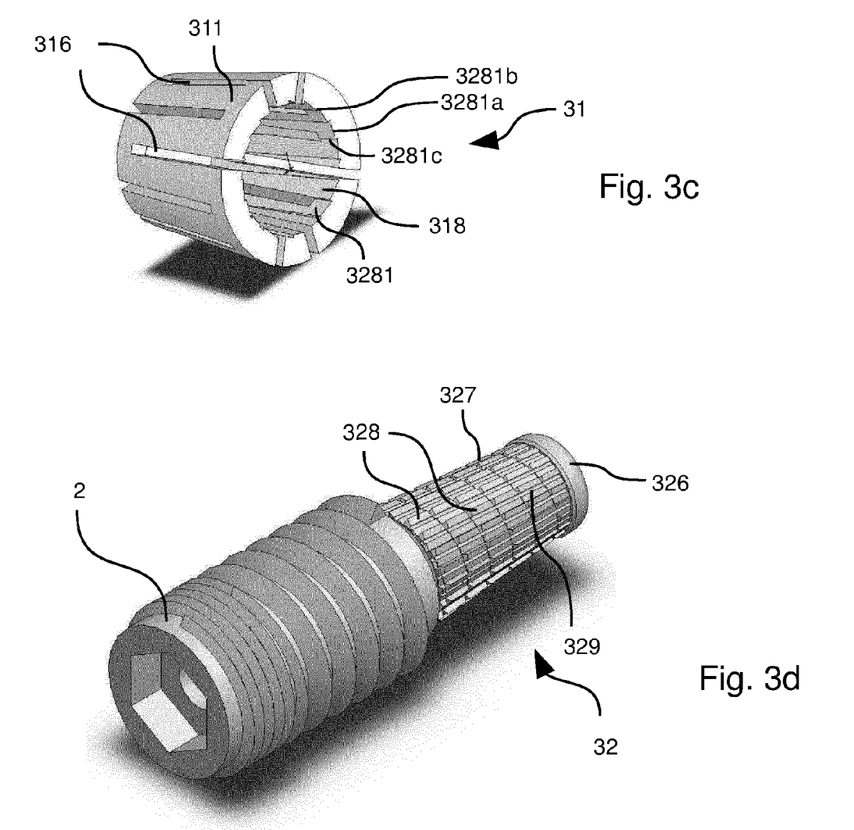
FIG. 3c represents a perspective view of the gripping portion of the endosseous implant according to the third embodiment of the invention.
FIG. 3d represents a perspective view of the endosseous implant without the gripping portion illustrating an expansion portion of the endosseous implant according to the third embodiment of the invention.

As illustrated in the example in FIG. 3c, it comprises longitudinal slots 316 opening up at either of the two longitudinal ends of the gripping portion 31, capable of allowing for an even more significant extension of said gripping portion, further to the elastic properties intrinsic upon the material used to make the gripping portion 31.

Although twelve slots are illustrated and described in FIG. 3c, these slots are not limited in number to that described and illustrated. It is therefore possible, without leaving the scope of the invention, to manufacture a gripping portion 31 with two or three slots or more.

In another example not represented herein, it comprises four elements connected in pairs by two slightly curved branches, capable of allowing for an even more significant extension of said gripping portion, further to the elastic properties intrinsic upon the material used to make the gripping portion 31.

To improve the grip of the implant in the osseous tissue, the gripping portion 31 comprises immobilising means rotationally and translationally immobilising the gripping portion 31 on all of part of its outer surface 311. So as not to overload the figures, the rotational and translational immobilising means are not represented.

In one example of embodiment of the immobilising means, said means are a plurality of blades or protrusions, randomly oriented, with a transversal cross-section preferably triangular in shape with a sharp cutting edge.

According to one characteristic of this embodiment, the engaging connection means 33 maintaining the expansion portion 32 within the gripping portion 31 are comprised from a helical connection between the outer surface 327 of the expansion portion 32 and the inner surface 318 of the gripping portion 31.

For example, the helical connection 33 is formed on the one hand at the outer surface 327 of the expansion portion 32 from a conical thread 331, preferably with a constant pitch preferably identical to the pitch of the thread 23 on the outer surface 24 of the body 2, and on the other hand, at the inner surface 318 of the gripping portion 31, from a tapping (not represented in the figures) with a complementing pitch.

In one specific embodiment, the outer surface 327 comprises dual conical threading offset by 180°.

The helical connection 33 causes the gripping portion 31 to rotate in a so-called screwing direction around the expansion portion 32, thus causing its translation along the longitudinal axis 11, towards the body 2.

Figure 3E:
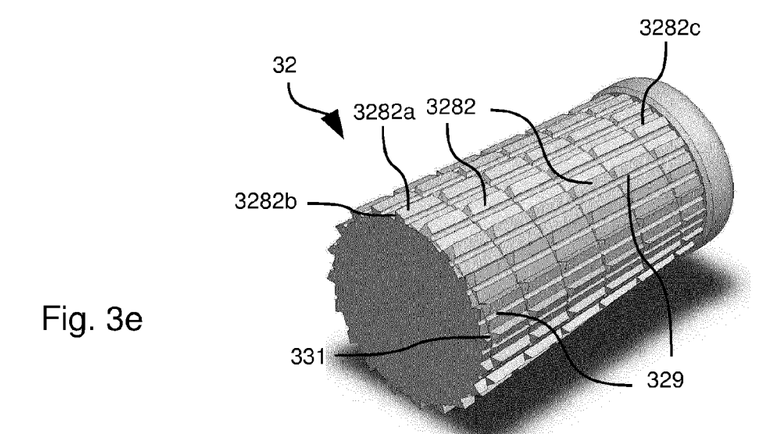
Figure 4A:
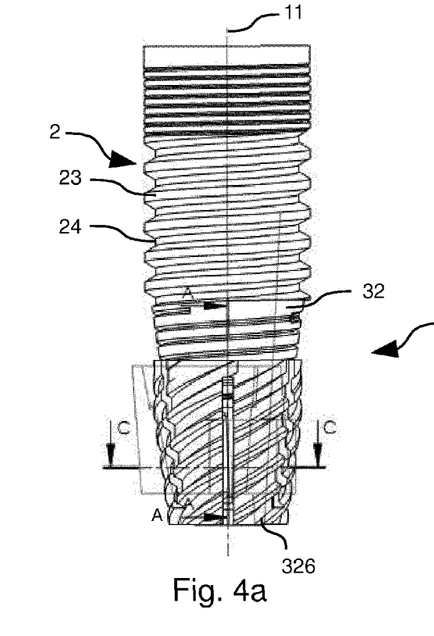
Figure 4B:
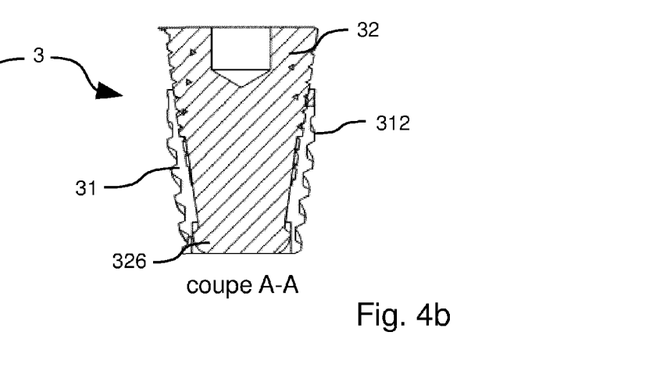
Figure 4C:
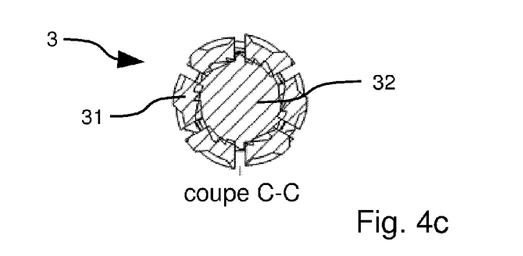
Figure 5A:
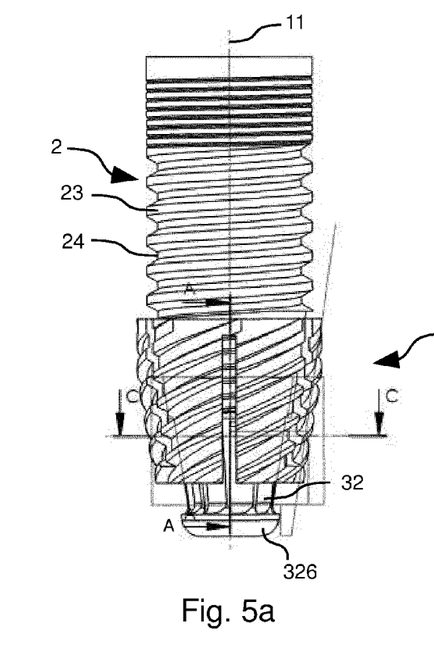
Figure 5B:
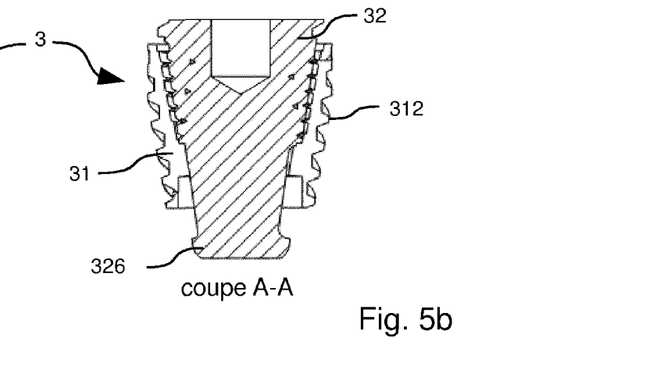
Figure 5C:
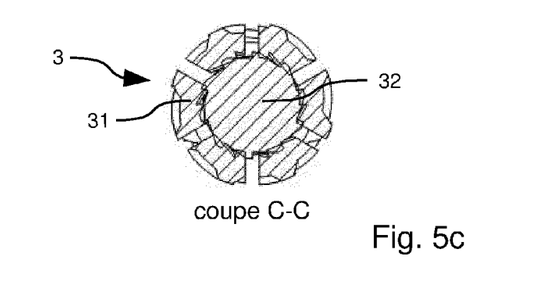

Preferably, the fastening device 3 also comprises, on the outer surface 327 of the expansion portion 32 and the inner surface 318 of the gripping portion 31, engaging reverse-lock means 328 as illustrated in FIGS. 3c, 3d and 3e, capable of preventing rotation between the gripping portion and the expansion portion in a direction opposite to that allowed by the helical connection and thus of rotationally blocking the implant. The reverse-lock means 328 prevent rotation between the two portions in a direction opposite to the screwing direction. Therefore, the implant cannot inadvertently become unscrewed.

In one example of embodiment of the reverse-lock means 328, said means are formed on the one hand, at the outer surface 327 of the expansion portion 32, by a first outer peripheral toothing 3282 and on the other hand, at the inner surface 318 of the gripping portion 31, by a second outer peripheral toothing 3281.

Said two outer peripheral toothings 3281, 3282 are designed to engage with each other, regardless of whether the implant is in its initial state, i.e. not extended, under extension, or in its extended state, i.e. locked in a position creating compression within the osseous tissue.

In one preferred embodiment of the invention, the outer peripheral toothing 3281 of the gripping portion 31 or respectively 3282 of the expansion portion 32, has a saw-toothed cross profile and asymmetrical sides, with upwards sloping sides 3281a or respectively 3282a and downwards sloping sides 3281b or respectively 3282b. Each upwards sloping side is connected to a downwards sloping side by a substantially sharp cutting edge 3281c or respectively 3282c. The teeth of the two outer peripheral toothings 3281, 3282 are positioned so that in the screwing direction, the gripping portion 31 is caused to rotate around the expansion portion 32, thus causing its translation along the longitudinal axis 11 of the implant.

The outer peripheral toothings 3281, 3282 are therefore positioned in relation to each other in a manner so as to only be able to move in a single direction of rotation in relation to each other.

During screwing, in the screwing direction, the upwards sloping sides 3281a of the gripping portion 31 slide against the upwards sloping sides 3282a of the expansion portion 32 to enable the relative rotational movement, and thus the translational movement along the longitudinal axis 11 of the implant, of the gripping portion 31 in relation to the expansion portion 32.

In the event of unscrewing, i.e. screwing in the direction of rotation opposite to the screwing direction, the downwards sloping sides 3281b of the gripping portion 31 abut against the downwards sloping sides 3282b of the expansion portion 32, thus blocking unscrewing movements.

In one example of embodiment of the teeth at the outer surface 327 of the expansion portion 32, the upwards sloping sides 3282a are positioned at an angle $\alpha$ in relation to a tangent to said outer surface, of between 0 and 45°. The downwards sloping sides 3282b are positioned at an angle $\beta$ in relation to a tangent to said outer surface, of between 55 and 90°.

In one example of embodiment of the teeth at the inner surface 318 of the gripping portion 31, the upwards sloping sides 3281a are positioned at an angle $\gamma$ in relation to a tangent of said inner surface, of between 0 and 45°. The downwards sloping sides 3281b are positioned at an angle $\delta$ in relation to a tangent to said inner surface, of between 55 and 90°.

The downwards sloping sides 3281b, 3282b each have a height such that, when the implant is in its maximum extended state, the downwards sloping sides 3281b of the gripping portion 31 abut against the downwards sloping sides 3282b of the expansion portion 32, thus blocking unscrewing movements. In a non-limitative example, this height is between 0.3 and 5 mm.

The fastening device 3 also comprises, on the outer surface 327 of the expansion portion 32, longitudinal grooves 329 capable of limiting tightening of the implant and thus of locking the compression of the mobile gripping portion 31.

In one preferred embodiment, the longitudinal grooves 329 are each comprised from a tooth at the level of an upwards sloping side 3282a. The longitudinal grooves 329 thus strengthen the locking of the implant in the screwing direction when compression is complete.

In the example in FIG. 3e, the longitudinal grooves 329 are substantially located halfway along the height of the upwards sloping side 3282a.

Figure 6A:
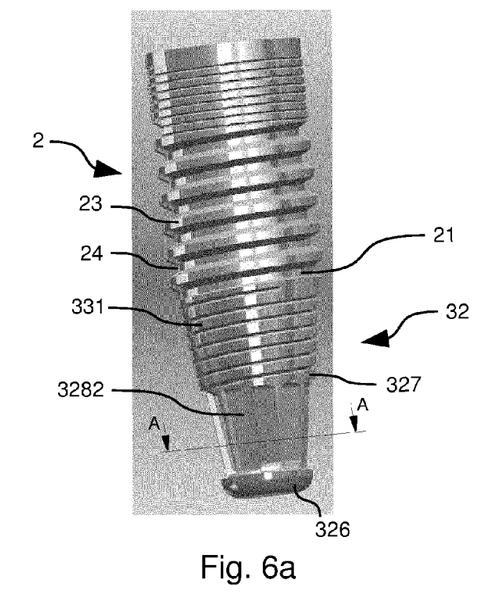
FIGS. 6a and 6b represent a perspective view of the implant without its gripping portion and a transversal cross-section at the level of the expansion portion according to an alternative of the third embodiment of the invention.
Figure 6B:
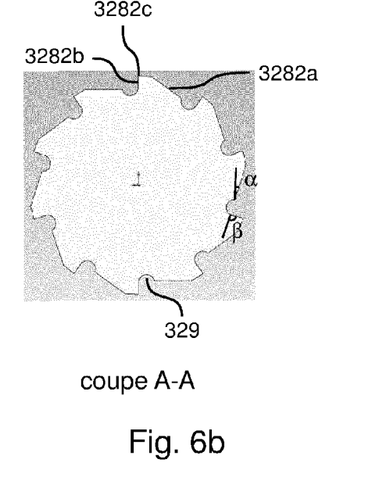
Figure 7A:
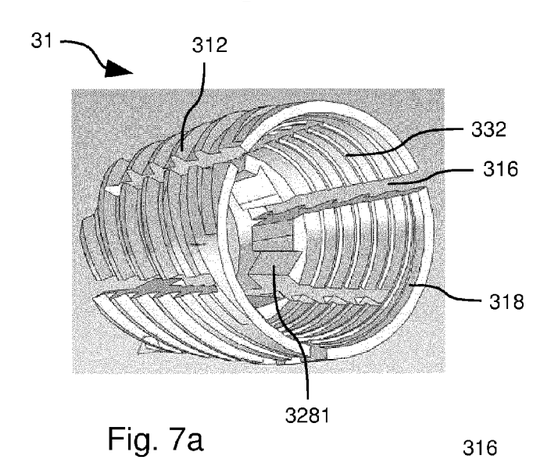
FIGS. 7a to 7c represent two perspective views and one transversal cross-section of the gripping portion associated with the expansion portion of the implant in FIGS. 6a and 6b, FIGS. 8a and 8b illustrate the implantation of the implant according to an alternative of the third embodiment of the invention in a housing of an osseous tissue, in an initial state and in an extended state.
Figure 7B:
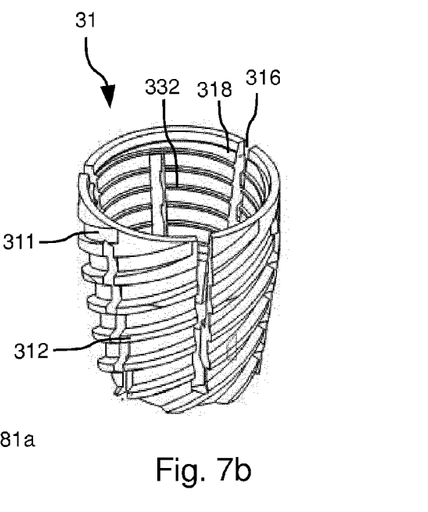
Figure 7C:
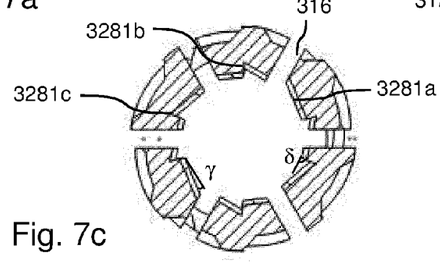
Figure 8A:
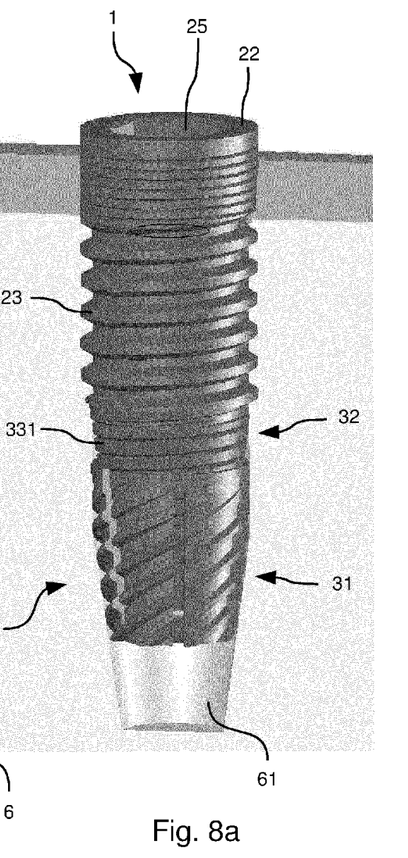
Figure 8B:
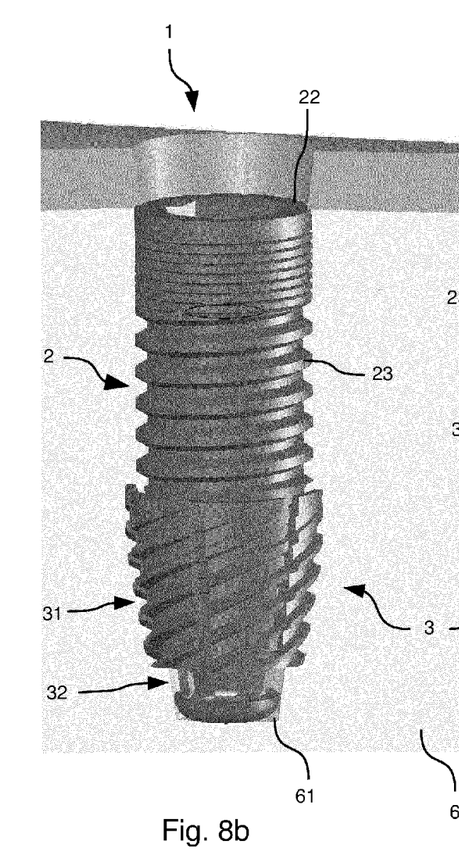

In the example in FIG. 6b, the longitudinal grooves 329 are substantially located at the base of the upwards sloping side 3282a.

The implant is thus immobilised both in translation by the immobilising means and in rotation in the screwing direction by the longitudinal grooves 329 and in the unscrewing direction by the reverse-lock means 328.

In the second embodiment illustrated in FIGS. 3a to 3e, the engaging connection means 33 interlock with the reverse-lock means 328.

Alternatively to this second embodiment of the fastening device illustrated in FIGS. 4a to 8b, the engaging connection means 33 no longer interlock with the reverse-lock means 328 but are disconnected therefrom to ease machining of the implant.

The expansion portion 32 keeps its frustoconical shape, narrowing from said endosseous end.

As illustrated in FIGS. 4a to 5c, the expansion portion 32 comprises on the one hand, at the endosseous end 32, the conical thread 331 of the helical connection 33, and on the other hand, at the shoulder 326, the outer peripheral toothing 3282, with a saw-toothed profile, of the reverse-lock means 328.

Advantageously, to accelerate the screwing of the implant into the housing, the conical thread 331 is a dual thread known in the prior art.

As illustrated in FIGS. 6a to 7c, the gripping portion 31 comprises on the one hand, at an end located near to the endosseous end when the gripping portion is positioned on the implant, the tapping 332 of the helical connection 33, and on the other hand, at an end located near to the shoulder 326 when the gripping portion is positioned on the implant, the outer peripheral toothing 3281, with a saw-toothed profile, of the reverse-lock means 328.

When the gripping portion 31 is positioned on the expansion portion 32 of the implant in an initial state:
  a portion of the tapping 332 of the gripping portion 31 is dampened in a portion of the thread 331 of the expansion portion 32,
  the outer peripheral toothing 3281 of the gripping portion 31 is facing the outer peripheral toothing 3282 of the expansion portion 32, with the upwards sloping side 3281a against the upwards sloping side 3282a.

Preferably, the gripping portion 31 of the implant in an initial state is dampened at the screwing location, substantially over one rotation.

In one example of embodiment of the immobilising means illustrated in figures such as 7a, 7b, 8a and 8b, said means are a thread 312 on the outer surface 311 of the gripping portion 31. Preferably, the thread 312 has a pitch substantially identical to that of the thread 23 on the outer surface 24 of the body 2.

Preferably, and unlike the thread 312 represented in the figures, the thread is a contra-rotating thread compared to the thread 23 on the outer surface 24 of the body 2 of the implant, to improve the anchoring effect.

Mode of Operation of the Second Embodiment of the Implant and its Alternative Embodiment The implant 1 (FIGS. 3a and 8a) is introduced into the housing 61 of the osseous tissue 6 by screwing the anchoring means 23 into the lateral walls 62 of said housing 61 using a suitable screwing tool. The implant is immobilised in translation.

When the extension means 322 abuts against the lower wall 63 of the housing 61, the practitioner continues to screw. Via the connection means 33 (helical connection), the gripping portion 31, by rotating in a screwing direction, moves in translation in relation to the expansion portion 32 along the longitudinal axis 11 towards the body 2 of the implant 1. This relative translational movement along the longitudinal axis 11 causes the slots to extend and thus causes the gripping portion to extend (FIGS. 3b and 8b) until it becomes anchored into the lateral walls 62 of the housing 61. Unscrewing is not possible due to the reverse-lock means 328. The implant is immobilised in rotation.

The screwing of the implant 1 into the housing 61 of the osseous tissue 6 advantageously generates the relative translational movement between the two portions.

The implant is thus immobilised both in translation and rotation.

Therefore, in this second embodiment of the implant, for an initial body diameter of 3.5 mm, an implant can be obtained, with the elastic properties of the zirconium gripping portion and after expansion, with a diameter at said gripping portion of 5 mm.

Advantageously, the different embodiments proposed of the invention improve the sealing and anchoring of the endosseous implant. There is no longer a need to wait six months for the bone to bond to the implant and a provisional prosthetic device may be directly installed on the implant a few hours after its implantation in the osseous tissue.

Furthermore, the different embodiments proposed are easy to manufacture, for example by machining, with desired manufacturing limits as large as possible without affecting the quality of the overall anchoring of the implant in the osseous tissue. Their manufacture therefore takes place at a low cost.

Another advantage of these different embodiments of the implant lays in the fact that it has an extended life in the patient's body.

Indeed, current implants need to be replaced every two years as the patient's bone structure changes and the implants become insufficiently anchored in said bone structure and can therefore be removed accidentally. With the different embodiments of the implant, the prosthetic device can be removed, the implant be re-screwed so as to widen the gripping portion 31 until the osseous tissue becomes re-compressed. The prosthetic device can then be reinstalled.

The different embodiments of the endosseous implants according to the invention are described hereinabove using the example of a dental implant, however in no way limit the scope of the invention.

The endosseous implant according to the invention can also be adapted to suit other applications, based on modifications capable of being implemented by one of ordinary skill in the art.

Figures 9A, 9B:
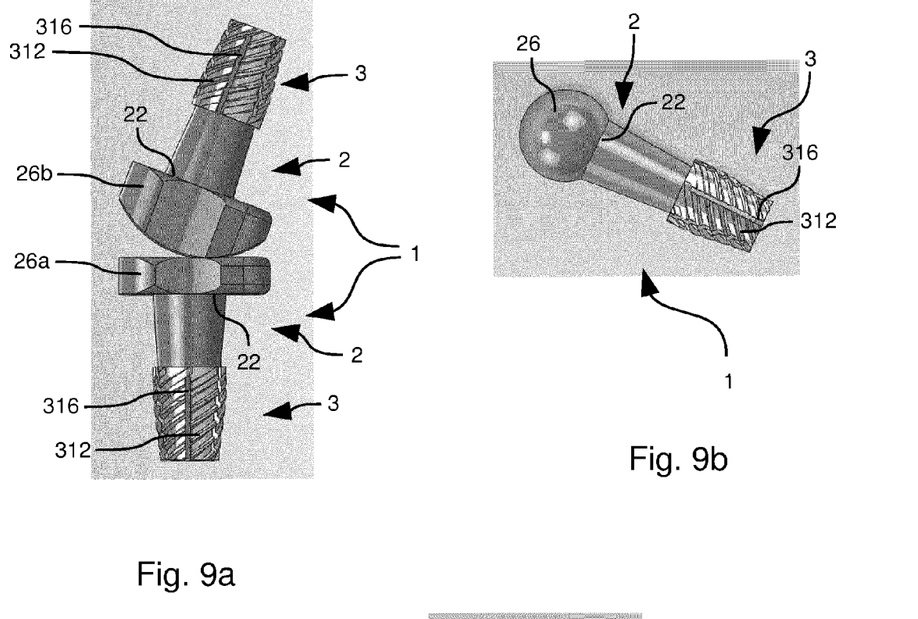
FIGS. 9a and 9b illustrate a hand or foot prosthesis produced using an implant according to the invention.

In one example of application illustrated in FIGS. 9a and 9b, the endosseous implant 1 is designed for the installation of a prosthetic joint in the hand or toe of a patient. The prosthetic joint is an artificial joint that replaces the joint damaged by worn cartilage, for example by arthritis. The joints targeted by such implants include:

for hands, distal or proximal interphalangeal joints, metacarpophalangeal joints, for feet, distal or proximal interphalangeal joints, metatarsophalangeal joints, For distal or proximal interphalangeal joints of the hand or foot, prosthesis comprises two endosseous implants, referred to as phalangeal implants, connected by a simple pivot connector, known in the prior art, as illustrated in FIG. 9a.

Each phalangeal implant comprises the body 2 and the fastening device 3.

In one example of embodiment, the bodies 2 of the phalangeal implants comprise anchoring means.

In another example of embodiment, as illustrated in FIGS. 9a and 9b and unlike dental implants, the bodies 2 of the phalangeal implants do not comprise anchoring means.

The fastening devices 3 comprise the gripping portion and expansion portion in addition to the engaging connection means and the reverse-lock means. Only the expansion portion 31 with its longitudinal slots 316 and the rotational and translational immobilising means 312 are visible in FIG. 9a.

The body 2 of one of the two phalangeal implants 1 comprises, at its exosseous end 22, a substantially flat plate 26a and the body of the second phalangeal implant 1 comprises, at its exosseous end 22, a substantially semispherical plate 26b to allow for sliding between the two implants.

Each implant comprises a longitudinal recess (not represented in FIG. 9a), preferably centred around the longitudinal axis of the implant, opening up at the exosseous end and allowing for the passage of a screwing tool of said implant.

The phalangeal implants are anchored into the osseous tissue via their respective fastening devices 3.

In a specific example of application illustrated in FIG. 9b, the prosthesis comprises, for metacarpophalangeal or metatarsophalangeal joints, an endosseous implant with a ball-and-socket connection, known in the prior art.

The implant comprises the body 2 and the fastening device 3.

As for phalangeal implants:
the fastening device 3 comprises the gripping portion and expansion portion in addition to the engaging connection means and the reverse-lock means. Only the expansion portion 31 with its longitudinal slots 316 and the rotational and translational immobilising means 312 are visible in FIG. 9b.

the implant comprises a longitudinal recess (not represented in FIG. 9b), preferably centred around the longitudinal axis of the implant, opening up into the spherical head, and allowing for the passage of a screwing tool of said implant.

According to two different examples of embodiment, the body 2 may or may not comprise anchoring means.

The body 2 of the implant 1 comprises, at its exosseous end 22, a spherical head 26 for allowing for a ball-and-socket connection with a hollow cup, generally hemispheric in shape, capable of being attached to the bottom of a cavity of the metacarpus.

The implant is anchored into the osseous tissue by the fastening device 3.

Mode of operation of the joint implants of the hand or foot in the example where the body 2 does not contain any anchoring means Each implant 1 is introduced and positioned in the housing previously built in the osseous tissue of the phalanx, without screwing as far as the lower wall. The practitioner introduces the screwing tool into the longitudinal recess and screws the implant. Via the engaging connection means, the gripping portion 31, by rotating in a screwing direction, moves in translation in relation to the expansion portion along the longitudinal axis 11 towards the body 2 of the implant 1. This relative translational movement along the longitudinal axis of the implant causes the slots to extend and thus causes the gripping portion to extend (FIGS. 3b and 8b) until it becomes anchored into the lateral walls 62 of the housing 61. Unscrewing is not possible due to the reverse-lock means 328. The implant is rotationally and translationally immobilised within the phalanx.

Figure 10:
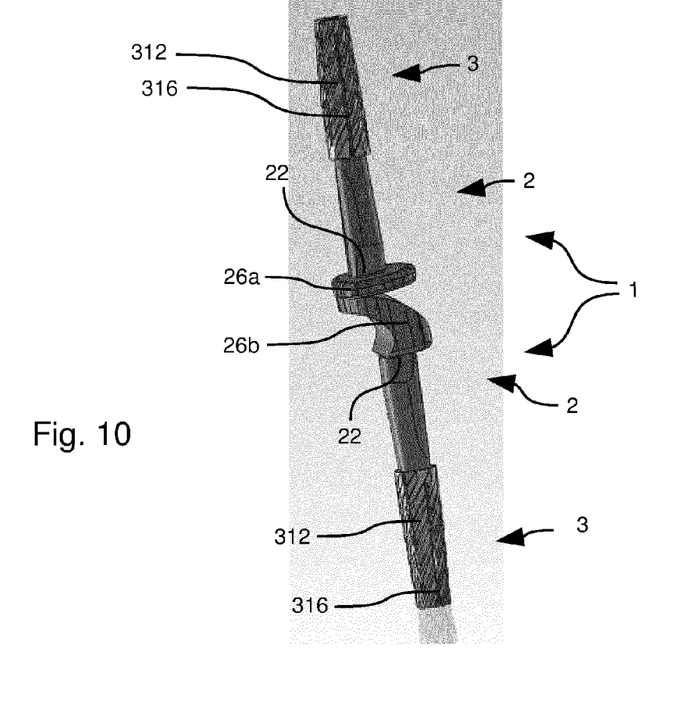
FIG. 10 illustrates a knee prosthesis produced using implants according to the invention.

In another example of application illustrated in FIG. 10, the endosseous implant 1 is designed for the installation of a patient's knee prosthesis.

The prosthesis comprises an endosseous implant 1, known as a femoral implant, and an endosseous implant 1, known as a tibial implant, connected together by a simple pivot connection, known in the prior art, as illustrated in FIG. 10.

Each tibial or femoral implant 1 comprises the body 2 and the fastening device 3.

According to two different examples of embodiment, the body 2 may or may not comprise anchoring means.

The fastening devices 3 comprise the gripping portion and expansion portion in addition to the engaging connection means and the reverse-lock means. Only the expansion portion 31 with its longitudinal slots 316 and the rotational and translational immobilising means 312 are visible in FIG. 10.

The body 2 of the tibial implant 1 comprises, at its exosseous end 22, a substantially flat plate 26*a* and the body 2 of the femoral implant 1 comprises, at its exosseous end 22, a substantially semi-spherical plate 26*b* to allow for sliding between the two implants.

Each implant comprises a longitudinal recess (not represented in FIG. 10), preferably centred around the longitudinal axis of the implant, opening up at the exosseous end, and allowing for the passage of a screwing tool of said implant.

The implants are anchored into the osseous tissue via their respective fastening devices 3.

Mode of operation of the knee implants in the example where the body 2 does not contain any anchoring means The femoral, or respectively the tibial implant 1 is introduced and positioned in the housing previously built in the osseous tissue of the femur, or respectively of the tibia, without screwing as far as the lower wall. The practitioner introduces the screwing tool into the longitudinal recess and screws.

Via the engaging connection means, the gripping portion 31, by rotating in a screwing direction, moves in translation in relation to the expansion portion along the longitudinal axis 11 towards the body 2 of the implant 1. This relative translational movement along the longitudinal axis of the implant causes the slots to extend and thus causes the gripping portion to extend (FIGS. 3*b* and 8*b*) until it becomes anchored into the lateral walls 62 of the housing 61. Unscrewing is not possible due to the reverse-lock means 328. The implant is rotationally and translationally immobilised in the femur or respectively in the tibia.

Figure 11:
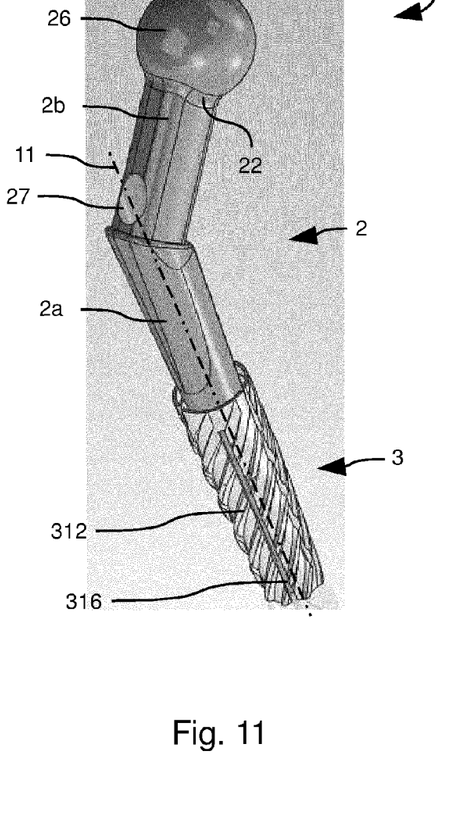
FIG. 11 illustrates a hip prosthesis produced using an implant according to the invention.
Figure 12:
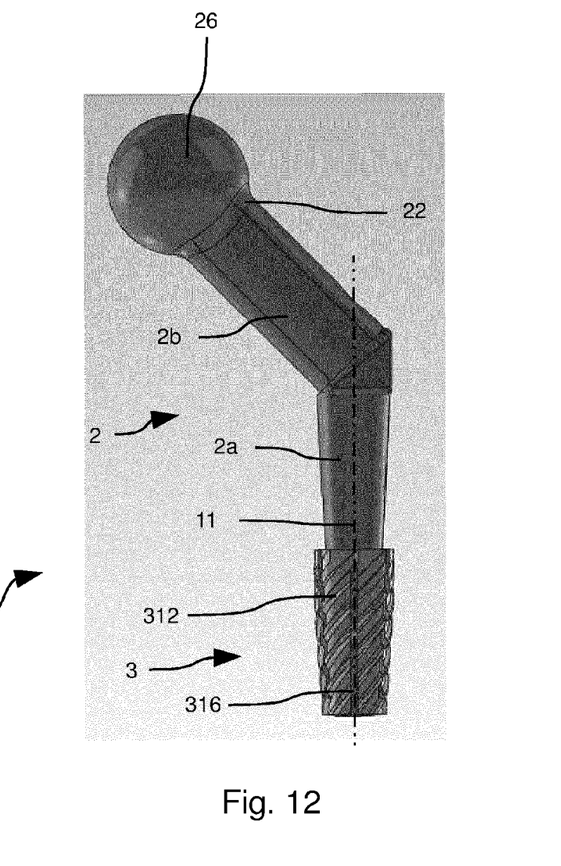
FIG. 12 illustrates a shoulder prosthesis produced using an implant according to the invention.

In another example of application illustrated in FIGS. 11 and 12, the endosseous implant 1 is designed for the installation of a hip prosthesis (FIG. 11) or shoulder prosthesis (FIG. 12) of a patient.

The prosthesis comprises an endosseous implant, known as a femoral implant 1 for the hip prosthesis and a humeral implant 1 for the shoulder prosthesis, with a ball-and-socket connection, known in the prior art.

The femoral implant or respectively the humeral implant comprises the body 2 and the fastening device 3. As for phalangeal implants, the fastening device 3 comprises the gripping portion and expansion portion in addition to the engaging connection means and the reverse-lock means. Only the expansion portion 31 with its longitudinal slots 316 and the rotational and translational immobilising means 312 are visible in FIG. 11.

According to two different examples of embodiment, the body 2 may or may not comprise anchoring means.

The fastening device 3 is designed to extend in the diaphysis of the femur or respectively of the humerus. The body 2 comprises a diaphyseal portion 2*a* designed to extend into the diaphysis of the femur or respectively of the humerus, along the extension of the fastening device 3, and a metaphyseal portion 2*b* designed to extend into the metaphysis of the femur or respectively of the humerus, with a predefined angle in relation to the longitudinal axis 11.

The body 2 of the femoral implant 1 or respectively of the humeral implant 1 comprises, at its exosseous end 22, a spherical head 26 for allowing for a ball-and-socket connection with a hollow cup, generally hemispheric in shape, capable of being attached to the bottom of a cavity of the ilium or respectively of the scapula.

The femoral implant or respectively the humeral implant comprises a longitudinal recess 27, preferably centred around the longitudinal axis of the implant, opening up into the metaphyseal portion 2*b*, and allowing for the passage of a screwing tool of said implant.

The femoral implant or respectively the humeral implant is anchored into the osseous tissue of the femur by the fastening device 3.

Mode of operation of the implant of the hip prosthesis or respectively of the shoulder prosthesis in the example where the body 2 does not contain any anchoring means The femoral, or respectively the humeral implant 1 is introduced and positioned in the housing previously built in the osseous tissue of the femur, or respectively of the humerus, without screwing as far as the lower wall. The practitioner introduces the screwing tool into the longitudinal recess and screws.

Via the engaging connection means, the gripping portion 31, by rotating in a screwing direction, moves in translation in relation to the expansion portion along the longitudinal axis 11 towards the body 2 of the implant 1. This relative translational movement along the longitudinal axis of the implant causes the slots to extend and thus causes the gripping portion to extend (FIGS. 3*b* and 8*b*) until it becomes anchored into the lateral walls 62 of the housing 61. Unscrewing is not possible due to the reverse-lock means 328. The implant is rotationally and translationally immobilised in the femur or respectively in the humerus.

The invention claimed is:

1. A system for securing dental implants in osseous tissue, the system comprising:
 a body defining a longitudinal axis having a distal end and a proximal end, the body comprising:
  a first portion, wherein the first portion is frustoconically shaped and located towards the distal end of the body, wherein the first portion is configured with a first plurality of threads and a first plurality of peripheral toothing; and
  a second portion, wherein the second portion is tubular and located towards the proximal end of the body, wherein the second portion is configured to attach a prosthetic device; and
 a sleeve having a distal end and a proximal end, the sleeve configured for insertion along the longitudinal axis of the body, wherein the distal end of the sleeve and the proximal end of the sleeve are configured to expand as the sleeve rotationally and longitudinally traverses the first portion of the body, the sleeve comprising:
  at least one transverse opening extending along the longitudinal axis from the distal end of the sleeve to the proximal end of the sleeve terminating prior to the proximal end of the sleeve;
  at least one transverse opening extending along the longitudinal axis from the proximal end of the sleeve to the distal end of the sleeve terminating prior to the distal end of the sleeve;

an inner surface, wherein the inner surface comprises a second plurality of threads such that the second plurality of threads are configured to engage the first plurality of threads of the first portion of the body, wherein the inner surface is further configured with a second plurality of peripheral toothing configured to interact with the first plurality of peripheral toothing such that rotational movement in a first direction is allowed and rotational movement in a second direction opposite to the first direction is prevented; and an outer surface, wherein the outer surface includes a plurality of protrusions, the plurality of protrusions configured such that upon the sleeve engaging the osseous tissue, the sleeve is prevented from moving in the first direction and the second direction.

2. The system of claim 1, wherein the sleeve is configured to expand to a diameter greater than a diameter of the second portion of the body.

3. The system of claim 2, wherein the expanded sleeve diameter is 40% greater than the diameter of the second portion of the body.

* * * * *